United States Patent [19]

Hidasi et al.

[11] Patent Number: 5,110,976

[45] Date of Patent: May 5, 1992

[54] INSECTICIDAL COMPOSITION COMPRISING MORE THAN ONE ACTIVE INGREDIENT

[75] Inventors: Gyorgy Hidasi, Budapest; Istvan Szekely, Dunakeszi; Bela Bertok; Sandor Zoltan, both of Budapest; Lajos Nagy, Szentendre; Antal Gajari, Budapest; Eva Somfai, Budapest; Agnes Hegedüs, Budapest; Laszlo Pap, Budapest; Rudolf Soos, Budapest; Erzsebet Radvany, Budapest; Sandor Botar, Budapest; Tamas Szabolcsi, Budapest, all of Hungary

[73] Assignee: Chinoin Gyogyszer es Vegyeszeti Termekek Gyara Rt., Budapest, Hungary

[21] Appl. No.: 696,580

[22] Filed: May 7, 1991

Related U.S. Application Data

[60] Continuation-in-part of Ser. No. 367,546, Jun. 16, 1989, Pat. No. 5,013,754, which is a division of Ser. No. 916,546, Oct. 15, 1986, Pat. No. 4,845,126.

[30] Foreign Application Priority Data

Jan. 16, 1985 [HU] Hungary ................................. 158/85
Jan. 8, 1986 [HU] Hungary ................................. 74/86

[51] Int. Cl.$^5$ ................... C07C 253/34; C07C 255/39
[52] U.S. Cl. ..................................... 558/407; 558/354; 558/355
[58] Field of Search ........................ 558/407, 354, 355

[56] References Cited

U.S. PATENT DOCUMENTS

| | | | |
|---|---|---|---|
| 4,997,970 | 3/1991 | Ager, Jr. ................ | 558/407 X |
| 5,013,754 | 5/1991 | Hidasi et al. ............ | 558/407 X |
| 5,028,731 | 7/1991 | Glenn .................... | 558/407 |

*Primary Examiner*—Joseph Paul Brust
*Attorney, Agent, or Firm*—Herbert Dubno; Jonathan Myers

[57] ABSTRACT

A process is disclosed for preparing a synergistic, crystalline product consisting of solely enantiomer pair 1RCisS and 1SCisR and enantiomer pair 1RTransS and 1STransR of cypermethrin in a 3:7 to 5:5 crystalline mixture, which comprises the steps of: (a) epimerizing an oily melt or a saturated solution of enantiomer pair 1RCisS and 1SCisR and enantiomer pair 1RTransS and 1STransR in a ratio other than 3:7 to 5:5, or a mixture of enantiomer pair 1RCisS and 1SCisR, enantiomer pair 1RTransS and 1STransR together with enantiomer pair 1RCisR and 1SCisS and enantiomer pair 1RTransR and 1STransS, said saturated solution including a protic or apolar, aprotic inert organic solvent by treating said oily melt or saturated solution with an organic or inorganic base at a temperature of −15° C. to 30° C. to precipitate crystals consisting solely of the 1RCisS and 1SCisR and the 1RTransS and 1RTransR enantiomer pairs in a 3:7 to 5:5 weight ratio; (b) isolating the precipitated crystals consisting solely of the enantiomer pairs 1RCisS and 1SCisR and 1RTransS and 1STransR at −10° to 30° C., optionally after inoculating the reaction mixture with a seeding crystal consisting of a mixture of the enantiomer pairs 1RCisS and 1SCisR and 1RTransS and 1STransR at a weight ratio of 3:7 to 5:5 before crystallization; and (c) repeating any of the above steps, if necessary.

6 Claims, No Drawings

INSECTICIDAL COMPOSITION COMPRISING MORE THAN ONE ACTIVE INGREDIENT

CROSS REFERENCE TO RELATED APPLICATIONS

This application is a continuation-in-part of Ser. No. 07/367,546 filed 16 Jun. 1989, now U.S. Pat. No. 5,013,754, which is a divisional of Ser. No. 06/916,546, filed Oct. 15, 1986, now U.S. Pat. No. 4,845,126, which is a National Phase of PCT HU 86/00004 filed 16 Jan. 1986; and is related to Ser. No. 07/371,650 filed 19 Jun.1989, now U.S. Pat. No. 4,963,584, which is a continuation of Ser. No. 06/918,129 filed 27 Oct. 1986, abandoned, which is a National phase of PCT HU 86/00003, filed 16 Jan. 1986; and based upon Hungarian Patent Applications 158/85 of 16 Jan. 1985 and 74/86 of 8 Jan. 1986.

This invention relates to insecticidal compositions comprising more than one pyrethroid active ingredient of the Formula (I)

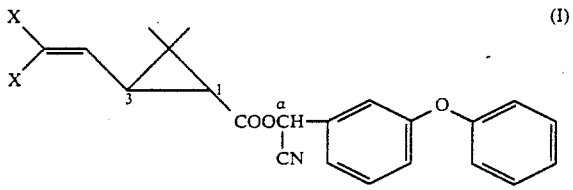

wherein X is chlorine or bromine, the use thereof, the active ingredients and a process for the preparation of the same.

BACKGROUND ART

In the present specification the spatial configuration of the substituents related to the chiral carbon atom denoted with "α" is characterized by "S" and "R", respectively The designations "cis" and "trans", respectively, mark the position of the substituents attached to carbon atom "3" of the cyclopropane ring related to the spatial configuration of the substituents of carbon atom "1". The absolute spatial configuration of the substituent attached to carbon atom "1" is denoted with the prefix "1R" and "1S", respectively.

In the present specification the various enantiomers and enantiomer-pairs are designated with the following abbreviations:

| | |
|---|---|
| Ia | mixture of 1RcisS and 1ScisR |
| Ib | mixture of 1RtransS and 1StransR |
| Ic | mixture of 1RcisR and 1ScisS |
| Id | mixture of 1RtransR and 1StransS |
| If | 1RtransR |
| Ig | 1RtransS |
| Ih | 1ScisR |
| Ii | 1StransR |

It is known that pyrethroids of the Formula (I) known under the generic name "cypermethrin" belong to the valuable family of synthetic pyrethroids and are useful as insecticides (Hungarian Patent No. 170,866). These compounds may be prepared by reacting m-phenoxy-benzaldehyde cyanohydrin with the corresponding cyclopropane carboxylic acid chloride in the presence of a base [Pestic. Sci. 6, 537 - . . . (1975)]. The product thus obtained consists of eight stereoisomers i.e. of a mixture of four enantiomer-pairs. If a 60:40 mixture of the corresponding trans and cis cyclopropane carboxylic acid chlorides is used, the mixture contains 18-19% of enantiomer-pair Ia, 21-22% of enantiomer-pair Ic, 26-27% of enantiomer-pair Ib and 33-34% of enantiomer-pair Id.

According to prior art the stereoisomers of cypermethrin show different biological activity. It is generally accepted that the activity of molecules comprising cis cyclopropane carboxylic acids is superior to that of the corresponding trans derivatives [Pest. Sci. 7, 273 (1976)].

In the comparative biological tests of various pyrethroids [Pest. Sci. 9, 112-116 (1978)] the cis and trans stereoisomers—including the cypermethrin stereoisomer-pairs—were evaluated together.

The comparative tests were carried out on Musca domestica L. and Phaedon cochleariae Fab species. Concerning the chloro derivatives from the trans isomers activity data of 1RtransS (Ig) and 1RtransR were disclosed. The said data show that—while the 1RtransS isomer possesses a strong activity—the 1RtransR isomer is considerably less active [according to the test the activity related to bioresmetrine (100) amounts to 1400 and 81, respectively, on Musca domestica and to 2200 and 110, respectively on Phae don cochleariae]. It was disclosed furtheron that the activity of a mixture of both tested isomers was lower than the calculated value. Thus the isomers showed an antagonism rather than the expected synergism and the rate of antagonism amounted to 1.42 and 1.46 on house fly and mustard beetle, respectively As a result of the said tests and publications the trans isomers and mixtures thereof were pushed to the background of biological interest and research was focused to active cis derivatives and mixtures thereof. This led to the development of alphamethrin (isomer mixture of 1RcisS and 1ScisR (Ia) of the chloro derivatives] and decamethrin [comprising the IRcisS isomer (If) of the bromo derivatives].

Similar data were set forth for the bromo derivative; on mustard beetle the rate of antagonism amounts to 1:48.

DISCLOSURE OF INVENTION

According to an aspect of the present invention there is provided a synergistic insecticidal composition containing more than one active ingredient and being harmless to the environment characterized by comprising in an amount of from 0.001 to 99% by weight a synthetic pyrethroid of the Formula (I)—namely substantially only the 1RtransS and 1StransR enantiomer-pair (Ib) out of the possible eight isomers—optionally in admixture with an amount of up to 100% by weight of one or more activator(s) and auxiliary agents(s), particularly antioxidants, stabilizing agents, wetting agents, emulsifying agents, dispersing agents, antifoam agents, diluents and/or fillers.

According to a preferred embodiment of this aspect of the present invention there are provided insecticidal compositions comprising an isomer mixture having a purity of at least 95%.

The said isomer mixture is a new crystalline substance, the physicochemical data thereof being disclosed in the Examples.

The present invention is based on the recognition that isomer-mixture Ib possesses useful and advantageous biological properties. This is surprising even if it is taken into consideration that in the field of pyrethroids of the Formula (I) extended experimental work was accomplished and a number of publications and patents were published.

Thus the present invention is based on the recognition that when using a combination of the 1RtransS isomer Ig [being the most active trans isomer of the compounds of the Formula (I)] and the 1StransR isomer Ii (being ranged among the less active isomers from the remaining seven isomers) no antagonism characteristic of the earlier published isomer-pairs is observed.

Moreover a synergistic effect occurs over the additive effect of the pure Ig and Ti isomers when used per se.

The above recognition enables a new type of selection from the isomers of synthetic pyrethroids in order to develop a new active ingredient type having outstanding properties. The said new active ingredient shows various advantages over hitherto known isomer selections:
lower toxicity on warm-blooded species and humans;
more economical manufacturing process;
smaller damage caused to useful parasites and bees.

A significant and decisive advantage of the isomer-mixture Ib of the present invention is that it causes no allergy and skin diseases which were generally observed on the use of the corresponding cis cypermethrin isomers of similar activity.

The synergistic activity of the components of the isomer-mixture Ib is even more surprising as no similar synergism takes place between the components of the isomer mixture Ia.

According to aspects of the present invention there is provided the selected isomer pair, at insecticidal composition comprising the same and a process for the preparation and the use thereof.

According to a still further aspect of the present invention there is provided a process for the preparation of the said new isomer pair. According to a particularly important aspect of the present invention there is provided a process for the preparation of the cypermethrin isomer-pair Ib which enables the highly economical preparation of an active ingredient having the same order of activity as the active ingredient which was hitherto available only by means of the very expensive isolation procedure of a pure and single cis isomer.

According to a further aspect of the present invention there is provided a synergistic insecticidal composition containing more than one active ingredients and being harmless to the environment characterized by comprising in an amount of from 0.001 to 99% by weight a synthetic pyrethroid of the Formula (I)—namely substantially only the 1RtransS and 1StransR enantiomer-pair (Ib) out of the possible eight isomers—optionally in admixture with an amount of up to 100% by weight of one or more activator(s) and auxiliary agents(s), particularly antioxidants, stabilizing agents, wetting agents, emulsifying agents, dispersing agents, antifoam agents, diluents and/or fillers.

According to a further aspect of the present invention there is provided an isomer mixture Ib having a purity of at least 95% and comprising the 1RtransS and 1StransR enantiomer-pair of the Formula (I).

The physical constants of the said enantiomer-pair are as follows:
IR/KBr/$\nu_{c=o}$=1735 cm$^{-1}$
NMR/CDCl$_3$/$\delta$/ppm/ =1.22, 1.27 CMe$_2$; 1.69d 1H Cl; 2.32 m 1H C3; 5.6, d. 1H Cl'; 6.39 s 1H alphaproton.

The said pure enantiomer-pair is a white crystalline material, never described in the prior art according to our best knowledge. The melting point of the 1:1 mixture of the isomers amounts to 81.0°–81.5° C. it is to be noted that the components Ig and Ti of the isomer-pair are not crystalline per se. Accordingly in addition to biological and economical advantages the combination of the present invention facilitates the process of manufacture, the formulation procedure, storing and method of treatment as well.

The isomer-pair Ib of the present invention is superior to the known combinations from the point of view of side effects, too. The new isomer-pair of the present invention has a very low toxicity on bees and does not damage useful entomophages and parasites (see biological Examples 4 and 5). This is due to the repellant effect, preferable persistence and suitable inherent activity of the active ingredient. As a result of the above advantageous properties the insecticidal composition of the present invention may be useful in integrated plant protecting technology / IPM - Integrated Pest Management/.

The present invention is based on the further recognition that the enantiomer-pair of the present invention has substantially the same insecticidal activity as the enantiomer-pair Ia but is significantly less toxic on warm-blooded species. This is clearly substantiated by the selectivity index (7800) being the quotient of approximative LD$_{50}$ toxicity values on rates (5000 mg/kg) and house fly (0.64 mg/kg). The said selectivity index of the enantiomer-pair Ia amounts to 50/0.45=111.

The isomer-pair Ib is less toxic on parasites than the isomer-pair Ia and this is of particular importance. For this reason the insecticidal composition of the present invention may be used more safely, because on the edge of the sprayed area and after treatment (i.e. in area treated with a small concentration of the active ingredient) the parasites and bees are not killed. The repellant effect of the isomer-pair Ib is outstandingly good, too.

The insecticidal compositions of the present invention comprising the isomer-pair Ib in admixture with known additives may be formulated in forms suitable for direct use.

The composition of the present invention may be ULV (ultra-low-volume) compositions, spray, dispersible powders, granules, wettable and other powders, stable emulsions, etc. The said compositions are suitable for the pesticidal treatment of vegetables, orchards, fields of cereals and other large scale cultures. Due to the low toxicity the compositions of the present invention are particularly suitable for combatting flying insects and pests having a hidden mode of life in households, stables and also for use in bathing of domestic animals and for the treatment of pasture.

According to a further aspect of the present invention there is provided the use of the said insecticidal compositions. It is preferred to use the said compositions under field conditions at a rate of 2-25 g of active ingredient per hectare.

The insecticidal compositions of the present invention may comprise in addition to the isomer-pair Ib activators and further synergists, e.g. piperonyl butoxide. The said additives strengthen the efficiency of the active ingredient without increasing the toxicity on warm-blooded species.

According to a preferred embodiment of the present invention there are provided dispersible granules comprising 1–99 % by weight of the active ingredient in admixture with 99-1% by weight of suitable additives. As auxiliary agent e.g. 0.1-1 % by weight of anionic and/or non-ionic surfactants, may be used, such as alkalisalts of alkyl-aryl sulfonic acids, alkali salts of condensation products of alkyl aryl sulfonic acids and formaldehyde, alkyl-aryl-polyglycol ether, sulfated long-chained alcohols, polyethylene oxides, sulfated fatty alcohols, fatty acid polyglycol esters and various other commercially available surfactants.

The insecticidal compositions of the present invention may also be formulated in the form of concentrates comprising preferably 5-50% by weight of the active ingredient in admixture with 50-95% by weight of additives which enable the formation of a stable emulsion when emulsifying the emulsion concentrate in or in the presence of water.

As additive 1-20% by weight of a tenside and/or 0.1-5% by weight of a stabilizing agent may be used and the mixture may be preferably filled up to 100% with an organic solvent.

It is preferred to use as tenside a mixture of anionic and non-ionic tensides having a HLB-value of 8-14. The following tensides may be preferably applied: calcium salts of alkyl aryl sulfonic acids, mono and diesters of phosphoric acid, nonyl and tributyl phenol polyglycol ethers, adducts of fatty alcohols and ethylene oxide, fatty acid polyglycol esters, ethylene oxide-propylene oxide block polymers, etc.

As solvent preferably mixtures of aromatic hydrocarbons (e.g. xylenes), cyclohexanol, butanol, methyl ethyl ketone, isopropanol etc., may be used.

The compositions of the present invention may also comprise further synergistics which enable the reduction of the amount of the active ingredient. For this purpose preferably piperonyl butoxide may be applied.

According to a further aspect of the present invention there is provided a process for the preparation of a product comprising substantially only the enantiomer-pair 1RtransS+1StransR (Ib) out of the eight possible isomers of the compounds of the Formula (I) from mixtures comprising other isomers of further components, too.

The enrichment of cypermethrin mixtures in isomers having presumably a higher activity is described in several patent specifications. According to a patent publication [C.A. Vol. 95, (1981), Japanese Pat. KOKAI No. 57755/81] a crystalline cypermethrin isomeric mixture comprising 86.9% of Ic, 9.5% of Ia and 5.6% of Ib+Id is prepared by seeding a mixture comprising 53.5% of Ic, 38.7% of Ia and 7.8% of Ib+Id. In this case it was expected that the biological activity of the compounds remaining in the mother-lye would be higher.

It is the object of the other known procedures, too, to prepare cis isomer-pairs or substances enriched in cis isomer-pairs. According to a known process a mixture of enantiomer-pairs Ia and Ic is subjected to epimerization to convert the Ic enantiomer-pair into Ia enantiomer-pair and to produce the known alphamethrin and decamethrin, respectively, by asymmetrical transformation [Chem. and Ind., Mar. 19, 1985, 199-204; British patent Application No. 80 13308; EP No. 0 067 461; Dutch Patent No. 888 431, see Derwent 79766D].

The prior art is silent in teaching any methods directed to the preparation of trans isomers.

According to a further aspect of the present invention there is provided a process for the preparation of an isomer mixture Ib consisting substantially of only the enantiomer-pair 1RtransS and 1StransR—i.e. substantially only two out of the eight possible isomers of the compounds of the Formula (I)—from mixtures comprising also other isomers of the Formula (I) which comprises:

a) preparing a saturated solution from a mixture comprising the desired isomers in admixture with further possible isomers with a protic or apolar aprotic inert organic solvent, seeding the solution with a seeding crystal consisting of the enantiomer-pair 1RtransS+1StransR and isolating the precipitated crystals at a temperature between +30° C. and −30° C.; or b) seeding a melt of a mixture comprising the desired isomers in admixture with further possible isomers at a temperature between 10° C. and 60° C. with a seeding crystal consisting of the 1RtransS+1StransR enantiomer-pair, crystallizing at a temperature between 30° C. and −10° C., and if desired suspending the mixture thus obtained in a protic or apolar aprotic organic solvent at a temperature between −10° C. and −20° C. and isolating the separated crystals; or c) subjecting a mixture comprising the desired isomer-pair Ib in admixture with further possible isomers to chromatography in an organic solvent preferably on a silica gel or Kieselguhr adsorbent; or d) dissolving a mixture comprising trans isomers of the compounds of the Formula (I) in a protic or apolar aprotic solvent, seeding the solution with a seeding crystal consisting of the enantiomer-pair 1RtransS+1StransR (Ib), isolating the precipitated crystalline product Ib, and thereafter if desired epimerizing the mixture comprising Ib+Id being present in the mother-lye with an organic or inorganic base and if desired repeating the said step and/or the crystallizing step; or e) dissolving the mixture comprising the trans isomers in a secondary or tertiary organic amine base comprising 4-9 carbon atoms-optionally by adding an organic solvent—and seeding the solution thus obtained with a seeding crystal consisting of 1RtransS+1StransR isomers and thereafter isolating the precipitated crystals.

According to variants a) and e) of the process of the present invention one may preferably proceed by using a $C_{1-12}$ hydrocarbon, $C_{1-6}$ chlorinated hydrocarbon, $C_{1-5}$ dialkyl ether or $C_{1-10}$ alcohol as organic solvent. The said solvents may be straight or branched chained, and cyclic and alicyclic, respectively.

It is preferred to carry out seeding with a seeding crystal in the presence of an antioxidant—particularly tertiary butyl hydroxy toluene or 2,2,4-trimethyl-quinoline—and to use ethanol, isopropanol petrolether or hexane as solvent.

According to variant d) of the process of the present invention it is preferred to use a $C_{4-10}$ alkane, $C_{5-10}$ cycloalkane, $C_{1-8}$ alkanol and/or $C_{5-8}$ cycloalkanol or a mixture thereof as solvent. One may particularly advantageously use hexane, petrolether, cyclohexane, methanol, ethanol or isopropanol.

In the epimerization step ammonia, secondary or tertiary alkyl amines or cyclic amines may be used as basic substance. Thus one may preferably use triethyl amine, diethyl amine, morpholine, pyrrolidine, piperidine, diisopropyl amine, ephedrine, triethylene diamine, benzyl amine, n-butyl amine, secondary butyl amine, tetrabutyl ammonium hydroxide, sodium hydroxide, potassium tertiary butylate, sodium isopropylate or an ion-exchanging resin comprising a quaternary ammonium compound or a catalytic amount of an amine having a large molecular weight.

As solvent it is preferred to use methanol, ethanol, isopropanol, petrolether or hexane.

The said reaction variants may be particularly economically used if the total manufacturing line comprises the use and preparation of isomers of the Formula (I) other than Ib, too.

If synthetic cypermethrin manufacturing process makes it possible and if it is the aimed object of the invention to manufacture only a mixture of trans cypermethrin by means of one of the esterifying procedures, variant e) of the process of the present invention is particularly suitable for the economical manufacture of isomer-pair Ib. According to the said variant e) namely the complete amount of the trans mixture is converted into the desired enantiomer-pair Ib.

According to variant e) it is preferred to use triethyl amine, morpholine, pyrrolidine, piperidine, diisopropyl amine, ephedrine or secondary butyl amine as organic amine base.

It was a pre-condition of the feasibility of variant e) to provide and prepare highly pure seeding crystals having a purity over 95% and melting above 80° C. from the non-crystallizing pure isomers Ii and Id. The enables the aimed directed asymmetrical transformation.

One may proceed furtheron preferably by dissolving the mixture in the amine in the presence of an organic solvent. For this purpose the solvents enumerated by variant a) may be used.

According to variant a) one may proceed by dissolving the isomer mixture of trans cypermethrins—comprising the 1RtransS, 1StransR, 1RtransR and 1StransS isomers—in triethyl amine. Crystalline starting materials are dissolved at a temperature between 40° C. and 70° C. and the solution obtained may be filtered. An oily cypermethrin mixture may be dissolved at room temperature as well.

Crystallization of the 1RtransS+1StransR isomer-pair may be carried out by seeding the solution at room temperature with crystals of a 1:1 mixture of the 1RtransS and 1StransR isomers (recommended purity 99.8%) and thereafter subjecting the mixture thus obtained to crystallization at a temperature between 0° C. and 20° C. with or without stirring. The precipitated crystals are separated by filtration or centrifuging and the mother-lye adhered to the surface of the crystals is washed off with an alkane (preferably a solvent of the cycloalkane type particularly petrolether). The united mother-lyes are completely concentrated. The said crystallization procedure may be repeated. The asymmetrical transformation may be preferably accomplished in a dry inert gas (preferably nitrogen) atmosphere.

According to the above process a 1RtransS+1-StransR isomer-mixture having a purity of about 95% may be prepared with a yield of 80% per step. The purity may be increased to 99-99.5% by means of further recrystallization from an alcohol, particularly isopropanol.

If the base serves as solvent, too, it is preferred to use an amine-base having a water content not higher than 0.2-0.4%. Cis isomer contaminations of the trans cypermethrin mixture used as starting material may decrease the yield.

INDUSTRIAL APPLICABILITY

The insecticidal compositions of the present invention are harmless to the environment and can be used particularly in household and stables for combatting flying insects and pests having a hidden mode of life and also for bathing domestic animals and for the treatment of pasture.

MODES OF CARRYING OUT THE INVENTION

Further details of the present invention are to be found in the following chemical and biological examples without limiting the scope of protection to the said Examples.

Chemical Examples

EXAMPLE 1

10 g of a cypermethrin mixture consisting of 18.2% of Ia, 21.8% of Ic, 26.8% of Ib and 33.2% of Id are dissolved in 50 ml of a 95:5 mixture of n-hexane and tetrahydrofuran. The solution is subjected to chromatography on a column comprising 500 g of silica gel G. 25 ml fractions are collected by using a 95:5 mixture of n-hexane and tetrahydrofuran as eluting agent. Fractions corresponding to an $R_f$ value of 0.2 are collected (as TLC running mixture a 95:5 mixture of n-hexane and tetrahydrofuran is used). The said fractions are evaporated in vacuo. The residue thus obtained (2.9 g) is dissolved in 29 ml of ethanol at 45° C. and crystallized at 0° C. The precipitated product is filtered off, washed twice with 10 ml of ice cold ethanol each and dried in vacuo. Thus 2.6 g of a white crystalline product are obtained mp: 80.2° C.

Analytical characteristic data:

$R_f$=0.2 (Kieselguhr G plate, 95:5 mixture of n-hexane and tetrahydrofuran)

IR /KBr/ $\nu_{c=o}$=1735 cm$^{-1}$

NMR /CDCL$_3$/δ/ppm/=1.22, 1.27, CMe$_2$; 1.69, d, 1H Cl; 2.32, m, 1H C3; 5.6, d, 1H Cl'; 6.39, s, 1H, C alphaproton.

EXAMPLE 2

To 10 g of a crystalline trans cypermethrin mixture (comprising 53.9% of 1RtransR and 1StransS isomers and 43.3% of Ig isomers according to gas chromatography) 15 ml of anhydrous triethyl amine are added. The mixture is heated under nitrogen and under constant stirring at 60° C., whereupon the solution is quickly filtered and cooled to 30° C. The clear colorless solution thus obtained is seeded with a seeding crystal of a 1:1 mixture of Ib isomers, cooled to room temperature and allowed to crystallize for a day. The mixture is filtered cold. The product is dried at room temperature Thus 8.4 g of a snow-white crystalline product are obtained Mp.: 79.5°-80.5° C. According to gas chromatography analysis the product comprises 95% of a 1:1 mixture of the desired Ib isomers. The mother-lye is evaporated. On repeating the above steps 1.05 g of white crystalline product are obtained as second crops, mp 79°-80° C.

The united product is recrystallized from 50 ml of isopropanol. 8.5 g of a snow-white crystalline product are obtained as first crops, mp.: 80.5° C., active ingredient content 98%. On further recrystallization 7.5 g of a crystalline product are obtained, mp.: 81.5° C., active ingredient content above 99.5%.

IR /KBr/ $\nu_{c=o}$=1735 cm$^{-1}$

NMR /CDCL$_3$/δ/ppm/ =1.22, 1.27, CMe$_2$; 1.69, d, 1H Cl; 2.32, m, 1H C3; 5,6, d, 1H Cl'; 6.39, s, 1H, C alphaproton.

EXAMPLE 3

100 g of an oily crude (purity 95%) trans cypermethrin mixture (comprising 48% of 1RtransR and 1StransS isomers and 47% of Ib isomers according to gas chromatography) are dissolved in a solution of 150 ml of anhydrous triethyl amine and 0.2 g of tertiary butyl hydroxy toluene under stirring. The solution is quickly filtered, seeded, twice crystallized and recrystallized in an analogous manner to Example 2. Thus 82 g of snow-white crystalline isomer pair Ib are obtained, mp.: 80°-80.5° C., active ingredient content 97.5%.

EXAMPLE 4

10 g of oily trans cypermethrin mixture (comprising 85% of 1RtransR and 1StransS isomers and 14% of Ib isomers) are dissolved in 15 ml of anhydrous triethyl amine under stirring at room temperature, whereupon the solution is filtered and crystallized as described in Example 2. Thus 8 g of snow-white crystalline isomer mixture Ib are obtained, mp.: 79°-80.5° C.

EXAMPLE 5

10 g of crystalline trans cypermethrin (comprising 52% of 1RtransR and 1StransS isomers and 47% of Ib isomer-pair) are dissolved in 15 ml of tri-n-propyl amine at 50° C. The solution is filtered, cooled to 30° C. and seeded with a seeding crystal consisting of a 1:1 mixture of the Ib isomers. The mixture is allowed to crystallize for 48 hours. Thus 8.2 g of a snow-white crystalline product are obtained, mp.: 78°-80° C. Purity 95% (according to gas chromatography analysis)

EXAMPLE 6

One proceeds according to Example 5 except that 15 ml of tributyl amine are used as base. Thus 7.5 g of snow-white crystalline isomer-pair Ib are obtained, mp.: 77°-79° C., purity 93%.

EXAMPLE 7

One proceeds according to Example 5 except that 15 ml of triisopropyl amine are used as base. Thus 7.5 g of snow-white crystalline isomer-pair Ib are obtained, mp.: 78°-80° C., purity 95.5%.

EXAMPLE 8

One proceeds according to Example 5 except that 15 ml of diisopropyl amine are used as base. Thus 8.0 g of snow-white crystalline isomer-pair Ib are obtained, mp.: 78°-80° C., purity 95.5%.

EXAMPLE 9

10 g of trans cypermethrin (comprising 48% of 1RtransR and 1StransS isomers and 49% of Ib isomer-pair) are dissolved in 50 ml of isopropanol under stirring and heating whereupon 2 ml of an aqueous ammonium hydroxide solution are added (specific weight 0.880 g/ml). The solution is seeded with seeding crystals of the isomer-mixture Ib, stirred at 20° C. for 24 hours, cooled to 0°-5° C., and stirring is continued at this temperature. The suspension is filtered, the product is washed with isopropanol and petrolether and dried. Thus 6 g of white crystalline isomer-pair Ib (1:1) are obtained, mp.: 78°-79° C., purity 92% (GC analysis). From the mother-lye 1.5 g of white crystalline product are obtained as second crops. mp.: 78°-79° C. The composition of the second crops is identical with that of the crystals of the first generation.

EXAMPLE 10

10 g of trans cypermethrin (comprising 54% of 1RtransR and 1StransS isomers and 45% of isomers Ib) are dissolved in 100 ml of petrolether (b.p.: 60°-80° C.) whereupon 1 ml of a 0.5 molar sodium carbonate solution and a 1:1 vol. mixture of water and methanol comprising 10 w/v of tetrabutyl ammonium bromide are added. The solution is seeded with a seeding crystal according to Example 2, allowed to crystallize for 4 days, filtered, washed with petrolether and dried. Thus 6.8 g of white crystalline isomer-pair Ib are obtained, mp.: 78°-80° C., purity 95%, (GC analysis).

EXAMPLE 11

10 g of crystalline trans cypermethrin (comprising 52% of 1RtransS and 1StransR isomers and 47% of 1RtransR and 1StransS isomers) are dissolved in 100 ml of petrolether at 50°-60° C. To the solution 0.02 g 2,6-di-tertiary butyl-4-methyl-phenol is added. After filtration the filtrate is seeded at 30° C. with seeding crystals consisting of a 1:1 mixture of the Ib isomers. Crystallization is accomplished as disclosed above. Thus 3.8 g of snow-white crystalline isomer-pair Ib (1:1) are obtained, mp.: 77°-79° C., purity 93%. On recrystallization from petrolether the melting point rises 80.5° C. The crystallization mother-lye is epimerized in a separate step.

EXAMPLE 12

10 g of crystalline trans cypermethrin (comprising 45% of 1RtransS and 1StransR isomers and 53% of 1RtransR and 1StransS isomers) are dissolved in 75 ml of isopropanol at 50°-60° C. The solution is treated in an analogous manner to Example 11. Thus 3.6 g snow-white crystalline isomer-pair Ib are obtained. According to gas chromatography analysis the purity of the 1:1 mixture amounts to 94%. Mp.: 80° C. Further recrystallization is accomplished as described in Example 2. Thus a product having an active ingredient content above 99% is obtained. The crystallization mother-lye is epimerized in a separate step.

EXAMPLE 13

Into an apparatus equipped with a stirrer the mother-lye obtained according to Example 11 (a solution enriched in isomer Id) is introduced and 1 g of Dowex Type 2×4 mesh (serva) basical ion-exchanging resin are added. The heterogenous suspension is stirred at 40° C. for 12 hours, filtered, washed twice with 2 ml of isopropanol each. According to gas chromatography the solution comprises 41% of Ib isomer-pair and 46% of Id isomer. The solution is evaporated and crystallized as described in Example 11.

EXAMPLE 14

One proceeds according to Example 13 except that petrolether is used as solvent. According to gas chromatography analysis the solution comprises 39% of Ib isomer and 56% of the 1RtransR and 1StransS isomers.

EXAMPLE 15

10 g of colorless oily cypermethrin (comprising 30% of Ib, 31% of Id, 18% of Ia and 21% of Ic) are seeded with seeding crystals of a 1:1 mixture of the Ib isomers and allowed to crystallize at 7° C. for a week. The viscous crystalline oil obtained is cooled to −15° C., suspended in 10 ml of a 1:1 mixture of isopropanol and diisopropyl ether cooled to −15° C. and filtered cold. The crystals thus obtained are washed with 5 ml of ice cold isopropanol and dried at room temperature. Thus 2 g of white crystalline product Ib are obtained, mp.: 78°-80° C., purity 96% (GC). On recrystallization from 13 ml of hexane 2.25 g of a snow-white crystalline product are obtained, mp.: 80°–81° C., active ingredient content 99%.

EXAMPLE 16

10 g of Cypermethrin (comprising 30% of Ib, 31% of Id, 18% of Ia and 21% of I c) are dissolved in 100 ml of warm isopropanol whereupon 0.02 g of 2,5-di-tertiary butyl-4-methyl-phenol is added. The solution is clarified with 0.2 g of charcoal, filtered warm and the filtrate is seeded at 30° C. with a seeding crystal consisting of a 1:1 mixture of the Ib isomers. The mixture is allowed to crystallize at 10° C. for 24 hours, at 0° C. for 48 hours and finally at −5° C. for 24 hours (crystallization is accomplished so that an oily separation of the product should be avoided). The crystals are filtered cold, washed with isopropanol and dried at room temperature. Thus 2.6 g of snow-white crystalline Ib isomer-pair (1:1) are obtained, mp.: 78°–80° C., purity 95%. On recrystallization from hexane 2.3 g of a snow-white crystalline product are obtained, mp.: 80°–81° C., active ingredient content 99%.

Formulation Examples

EXAMPLE 17

Emulsifiable concentrates (EC) are prepared by admixing the following components:

| Component | Amount, kg/kg |
|---|---|
| 10 EC | |
| Isomer-pair Ib | 0.105 |
| Cyclohexanol | 0.290 |
| Atlox 3386 B | 0.020 |
| Atlox 3400 B | 0.045 |
| Odorless mineral oil | 0.540 |
| 5 EC | |
| Isomer-pair Ib | 0.050 |
| Cyclohexanol | 0.290 |
| Atlox 3386 B | 0.020 |
| Atlox 3400 B | 0.045 |
| Odorless mineral oil | 0.595 |

In a dose of 20 g of active ingredients/ha the composition 5 EC gives the same protection against Colorado beetle as a preparation of identical composition but comprising isomer Ia (alphamethrine composition).

EXAMPLE 18

A solution of 1.5 g of isomer-pair Ib and 1.5 g of fatty alcohol polyglycol ether is homogenized in a powder homogenizer with 30 g of synthetic silicic acid (Wessalon S), 60 g of talc (pH 7.1), 5 g of saccharose and 3.35 g of dodecyl benzene sulfonic acid. Thus a thin flowing powder is obtained.

EXAMPLES 19

20 g of isomer-pair Ib are diluted with 2 g of ethanol. The solution is admixed in a powder homogenizer with 5 g of calcium lignosulphonate, 5 g of nonyl-phenyl polyglycol ether (EO=20) and 70 g of calcium carbonate. The product thus obtained is ground in an Alpine 100 type mill. According to CIPAC the floatability amounts to 81%; wetting time=18 seconds.

Biological Examples

EXAMPLE 21

The comparative activity tests of enantiomer-pairs Ia and Ib on bean weevil (Acanthoscelides obtectus), flour-beetle (tribolium confusum) and sheep maggot fly (Lucilia sericata) show that enantiomer-pair Ib is more active than enantiomer-pair Ia. The results are summarized in Table I

TABLE 1

| Species | Enantiomer Pair | Dose (mg/disc) | | | | | |
|---|---|---|---|---|---|---|---|
| | | 0.02 | 0.07 | 0.22 | 0.67 | 2.0 | 6.0 |
| | | Mortality % | | | | | |
| A. Obtectus | Ia | 10 | 37 | 63 | 100 | 100 | 100 |
| (imago) | Ib | 32 | 55 | 87 | 100 | 100 | 100 |
| T. confusum | Ia | 0 | 18 | 51 | 100 | 100 | 100 |
| (imago) | Ib | 14 | 73 | 100 | 100 | 100 | 100 |
| L. sericata | Ia | 0 | 30 | 29 | 57 | 60 | 65 |
| (imago) | Ib | 22 | 55 | 70 | 75 | 100 | 100 |

The test is carried out as follows:

The stereoisomers are dissolved in a 1:2 mixture of mineral oil and acetone and filter paper discs (Whatman No. 1., diameter 9 cm) are impregnated with the corresponding dosage of the solution of the active ingredient. The acetone is allowed to evaporate and the insects are examined on filter paper discs placed into Petri-dishes. Three parallels are used for each dose and 15 animals are placed in each Petri-dish. Mortality rate is determined after 24 hours. The corrected mortality % data are calculated by means of the Abbot formula.

EXAMPLE 21

In Table 2 the synergism between the stereoisomers of the enantiomer-pair Ib is proved. The test is carried out on T. confusum and the following results are obtained by the contact method for various active ingredient doses.

TABLE 2

| Dose (mg/disc) | 0.11 | 0.33 | 1.00 | 3.00 |
|---|---|---|---|---|
| | Mortality % | | | |
| 1StransR Ii | 0 | 0 | 71 | 90 |
| 1RtransS Ig | 80 | 94 | 100 | 100 |
| Ib enantiomer-pair | 90 | 100 | 100 | 100 |

The test is carried out according to the method described in Example 20.

EXAMPLE 22

In Table 3 the $LD_{50}$ values of the Ig and Ii isomers and those of the Ib isomer-pair are disclosed. The data are topically measured.

TABLE 3

| Cypermethrin Stereoisomers | $LD_{50}$ (ng/insect) T. Confusum | | | $LD_{50}$ (ng/insect) Musca domestic | | |
|---|---|---|---|---|---|---|
| | measured | expected | synerg. factor | measured | expected | synerg. factor |
| Ig 1RtransS | 73.6 | — | — | 13.4 | — | — |
| Ii StransR | 1291.8 | — | — | 141.9 | — | — |
| Ib | 51.9 | 139.3 | 2.68 | 12.8 | 24.5 | 1.92 |

The above data prove the synergism between the trans isomers on both species.

The tests are carried out as follows;

a) *Musca domestica*

The active ingredients are dissolved in 2-ethoxyethanol (cellosolve) and 0.3 µl droplets of the solutions are applied onto the dorsal cuticulum of 3-5 days' old female house flies. 10 animals are used and 2 parallels are carried out for each dose. The tests are carried out for 5 dose levels between activity limits of 0% and 100%. After treatment the flies are placed into glass vials. Mortality is determined after 24 hours. Data are transformed to $\log_{10}$ dosage and probit mortality. $LD_{50}$ and confidence interval values are calculated by linear regression analysis of the log-probit data. The expected values required for the calculation of synergism are obtained by means of harmonic average. The synergistic factor is the quotient of the expected and measured values.

b) *T. confusum*

The active ingredients are dissolved in 2-ethoxyethanol and 0.3 µl droplets of the solutions are applied onto the abdominal side of 1-2 weeks' old imagos. Treatment is carried out with 2 parallels and 20 animals for each dose by using 5 dose levels in the range between activity limits of 0% and 100%. Evaluation and determination of $LD_{50}$ values and synergistic factors are carried out as described in Example 21.

EXAMPLE 23

Residual contact test on adults of *Apbidinus matricanae*

Adults of *A. matricariae* are exposed to residues of the active ingredients freshly applied on glass plates forming cages then the survivors are counted.

Treatments: test products(s) and control treated with water.

Replicates: at least 3. Plot size (net) 1 cage.

Parasites of known age 24 hours are used.

The products are applied at 5-1 ppm concentration, to each of the glass plates.

10 females of *A. matricariae* are introduced into each cage and supplied with honey as food. The number of females surviving exposure is determined after 1.5 and 24 hours, in independent runs. Total number of survivors is calculated for each cage.

The results are summarized in Table 4.

TABLE 4

| | Concentration | | | |
|---|---|---|---|---|
| | 5 ppm | | 1 ppm | |
| | 1h | 1h | 5h | 24h hours |
| | | mortality % | | |
| Ia | 100 | 100 | 100 | 96 |
| Ib | 100 | 0 | 75 | 88 |
| control | 0 | 0 | 0 | 1.5 |

EXAMPLE 24

Direct contact test of pupae of *A. matricariae*

Mature pupae of *A. matricariae* on paprika leaves in Petri dishes are exposed to a direct spray of the active ingredients.

Two or three days before emergence paprika leaves with parasitized pupae are used. The leaves are laid on filter paper in a plastic Petri dish The filter paper is moistened.

Application of treatment: See Example 23.

The pieces of leaf are transferred after treatment to clean Petri dish bottoms The trays are stored in a clinic chamber at 20° C. temperature, 70% relative humidity and a light-dark cycle of 18-8 h. Surviving pupae hatch after 2-3 days. The numbers of hatched and dead pupae are counted. Results are shown in Table 5.

TABLE 5

| | Concentration (ppm) | | | |
|---|---|---|---|---|
| | 30 | 10 | 5 | 1 |
| | | mortality % | | |
| Ib | 61.0 | 0 | 0 | 0 |
| deltametrin | 75.0 | 33.0 | 0 | 0 |
| control | 0 | 0 | 0 | 0 |

EXAMPLE 25

The active ingredients are dissolved in 2-ethoxyethanol and 0.3 1 droplets of the solutions are applied onto the abdominal sterna of potato beetle (*Leptinotarsa decemlineata*) imagos. The treatments are carried out by using two parallels and 10 insects for each dose. After treatment the insects are placed into Petri-dishes and mortality is determined after 48 hours The results are set forth in Table 6.

TABLE 6

| | Dose (µg/insect) | | | |
|---|---|---|---|---|
| cypermethrin | 0.05 | 0.10 | 0.20 | 0.40 |
| enantiomers | | 24 hours' mortality % | | |
| Ib | 0 | 25 | 75 | 85 |
| cypermethrin | 0 | 20 | 45 | 75 |

EXAMPLE 26

*T. confusum* (confused flour-beetle) imagos are treated according to Example 20 and percental mortality is determined after 24 hours. The dose of piperonyl butoxide (referred to furtheron as "PBC") amounts to 0.5 mg/disc The results are disclosed in Table 7. It can be seen that enantiomer-pair Ib can be synergized at a higher level than isomer pair Ia.

TABLE 7

| | Dose (mg/disc) | | | | |
|---|---|---|---|---|---|
| Active | 0.4 | 0.2 | 0.1 | 0.05 | 0.025 |
| ingredient | | 24 hours' mortality % | | | |
| Ia | 96 | 53 | 12 | 0 | 0 |
| Ia + PBO | 100 | 58 | 16 | 0 | 0 |
| Ib | 100 | 85 | 51 | 10 | 0 |
| Ib + PBO | 100 | 91 | 68 | 39 | 9 |

EXAMPLE 27

The active ingredients are dissolved in 2-ethoxyethanol and the solutions are applied in the form of 0.2 µl droplets onto the back of fall webworm (*Hyphantria cunea*) of $L_7$–$L_8$ larvae stage. The treated worms are placed on strawberry leaves in Petri-dishes. The test is carried out by using 5 doses; 2 parallels and 10 insects for each dose. The killed worms are counted after 24 hours and the percental mortality rate is calculated The results are summarized in Table 8.

TABLE 8

| | Dose (µg/larvae) | | | | |
|---|---|---|---|---|---|
| Cypermethrin | 0.023 | 0.047 | 0.094 | 0.188 | 0.375 |
| stereoisomers | | 24 hours' mortality % | | | |
| Ib | 10 | 15 | 30 | 70 | 80 |
| cypermethrin | 0 | 0 | 25 | 50 | 75 |

EXAMPLE 28

From a 5 EC formulation according to Example 17 50-, 100-, 200-, 400-, 800- and 1600-fold diluted emulsions are prepared by diluting with water. 0.5 ml of the emulsions are sprayed onto glass plates whereupon after drying 10 Colorado beetles (*L. decemlineata*) imagos are placed on each glass plate and the insects are covered. The tests are carried out with 6 doses by carrying out 3 parallels for each dose. The killed insects are counted after 48 hours and the percental mortality rate is calculated. The results are shown in Table 9.

TABLE 9

| 5 EC formulation | Dilution | | | | | |
|---|---|---|---|---|---|---|
| | 1600x | 800x | 400x | 200x | 100x | 50x |
| | | | Mortality % | | | |
| cypermethrin | 0 | 17 | 33 | 50 | 67 | 83 |
| Ib | 0 | 13 | 37 | 57 | 87 | 100 |

EXAMPLE 29

The insecticidal effect is tested on been weevil (*Acanthoscelides obtectus*) imagos. The killed insects are counted after 24 hours and the percental mortality rate is calculated. The results are shown in Table 10.

TABLE 10

| 5 EC formulation | Dilution | | | | | |
|---|---|---|---|---|---|---|
| | 1600x | 800x | 400x | 200x | 100x | 50x |
| | | | Mortality % | | | |
| cypermethrin | 0 | 3 | 10 | 20 | 43 | 60 |
| Ib | 3 | 10 | 20 | 37 | 53 | 67 |

According to another aspect of the present invention there is provided an insecticidal composition containing more than one active ingredients which comprises as active ingredient in an amount of 0.001–99% by weight a synthetic pyrethroid of the Formula I—namely out of the eight possible isomers at least 95% of a 3:7–5:5 mixture of the enantiomer-pairs Ia:Ib, wherein Ia is 1RcisS+1ScisR and Ib is 1RtransS+1StransR—if desired in admixture with an activator and/or with an amount of up to 100% of an auxiliary agent, preferably an antioxidant, stabilizer, wetting agent, emulsifying agent, dispersing agent, antifoam agent, diluent, carrier, and/or filler.

The present invention is based on the discovery that the isomeric mixture Ia+Ib possesses valuable and advantageous biological properties. The said properties are surprising and unforeseen, although extended research work has already been performed in the field of pyrethroids of the Formula I and a number of publications and patents have been published.

It is known further that mixtures enriched in cis isomers can be prepared by means of crystallization from solutions comprising other isomers [C.A. 95, 1981; KOKAI No. 5775/81]. A substantially pure 1:1 mixture of the 1RcicS and 1ScisR isomers may be separated by using suitable solvents from a mixture comprising the other cis isomers too (British Patent Specification No. 2,064,528). The isomeric mixture Ia is described to be very active. Special, so-called "high cis" syntheses have been elaborated for the preparation of cis-cyclopropane carboxylic acid intermediates comprising cis isomers above a certain limit (about 50%), but these methods were rather expensive [Angew. Chem. i.e, 24, (11), 996 (1985)].

The present invention is based on the recognition that when using a combination of the 1RtransS isomer Ig (being the most active trans isomer of the compounds of the Formula I) and the 1StransR isomer Ti (being ranged among the less active isomers from the remaining seven isomers) no antagonism characteristic for the earlier published isomer-pairs is observed.

Moreover a synergistic effect occurs over the additive effect of the pure Ig and Ii isomers when used per se.

The above discovery enables a new type of selection from the isomers of synthetic pyrethroids in order to develop anew active ingredient type having outstanding properties. The said new active ingredient shows various advantages over hitherto known isomer selections:

lower toxicity on a warm-blooded species and humans;
more economical manufacturing process;
smaller damages caused to useful parasites and bees.

The present invention is based on the further discovery that the biological order of succession of biological activity previously observed for the individual isomers and the already known rules described for the isomer-pairs are not absolutely relevant for other isomer-pairs.

Thus we have tried to compare and simultaneously test the 1RtransS+1StransR enantiomer-pair Ib—which was found to be active by our experiments—with other isomers. The comparison has shown that synergism observed between the members of enantiomer-pair Ib (i.e. Ig and Ii) does not take place between the members of the corresponding cis enantiomer-pair Ia (i.e. If and Ih).

The present invention is based on the further discovery that while from the 1RcicS (If) and 1RtransS (Ig) isomers it is generally the If isomer which is the more active, on certain specii the biological activity of the enantiomer-pairs Ia and Ib proves to be opposite.

As a result of the aforesaid we have come to the surprising recognition that when using simultaneously the enantiomer-pairs Ia and Ib a synergistic effect is observed, i.e. the effect of the combination is superior to that of the additional effect of both enantiomer-pairs when used per se.

It has been found that the synergistic biological effect of mixtures Ia+Ib is not limited to such mixtures in which Ib is more active than Ia. Thus on Colorado potato beetle (Leptinotersa decemlineata) the use of the two enantiomer-pairs results in a significant synergism. The said results are disclosed in details in the examples.

Based on the above recognitions we have performed a new selection from the already known isomer mixtures and this led to the new composition of the present invention.

In addition to the synergistic effect the composition of the present invention has a number of further advantages too and for this reason it is an outstanding product. It is very important that the compositions of the present invention are less toxical towards mammals than the hitherto known compositions of similar efficiency. This is unambiguously proved by the so-called selectivity index (517 and 747, respectively) which is the quotient of the approximate $LD_{50}$ values measured on rats p.o. (280 and 355 mg/kg. respectively) and on house fly topically (0.54 and 0.48 mg/kg, respectively). The said selectivity index of Ia amounts to $50/0.45 = 111$.

The synergistic effect may be observed on mites too, thus the compositions are also useful as acaricidal agents. The compositions of the present invention show a low toxicity towards bees and do not damage useful entomophages and parasites. The said advantageous properties are due to the repellant effect, preferable persistence and suitable inherent activity of the active ingredient.

The above properties enable the use of the mixture of the enantiomer-pairs of the present invention in integrated plant protecting technology (IPM = Integrated Pest Management).

The economical advantages of the compositions of the present invention are at least as important as the biological efficiency. The preparation of a pure cis enantiomer-pair Ia requires very expensive synthetic methods or involves the loss of the trans components formed in the reaction mixture. On the other hand the present invention enables the use of practically all the components Ia and Ib from the reaction mixture formed by the most economical syntheses. (The rate of efficiency depends naturally on the particular syntheses used and the ratio for the components Ia and Ib of the mixture).

The insecticidal compositions of the present invention comprising the isomer-pairs Ia and Ib in admixture with known additives may be formulated in forms suitable for direct use.

The composition of the present invention may be ULV (ultra-low-volume) compositions, spray, dispersible emulsions, etc. The said compositions are suitable for the pesticidal treatment of vegetables, grape fields, orchards, fields of cereals and other large scale cultures. Due to the low toxicity the compositions of the present invention are particularly suitable for combatting flying insects and pests having a hidden mode of life in households, walls of stables for the treatment of pasture, etc.

According to a further aspect of the present invention there is provided the use of the said insecticidal compositions. It is preferred to use the said compositions under field conditions at a rate of 2-25 g of active ingredient per hectare.

The insecticidal compositions of the present invention may comprise in addition to the isomer-pairs Ia+Ib activators and further synergists, e.g. piperonyl butoxide. The said additives increase strengthen the efficiency of the active ingredient without increasing the toxicity on warm-blooded species.

According to a preferred embodiment of the present invention there are provided dispersible granules comprising 1-99% by weight of the active ingredient in admixture with 99-1% by weight of suitable additives. As auxiliary agent e g 0.1-1% by weight of anionic and/or non-ionic surfactants may be used, such as alkali salts of alkyl-aryl sulfonic acids, alkali salts of condensation products of alkyl aryl sulfonic acids and formaldehyde, alkyl-aryl-polyglycol ether, sulfated long chained alcohols, polyethylene oxides, sulfated fatty alcohols, fatty acid polyglycol esters and various other commercially available surfactants.

The insecticidal compositions of the present invention may also be formulated in the form of concentrates comprising preferably 5-50% by weight of the active ingredient in admixture with 50-95% by weight of additives which enable the formation of a stable emulsion when emulsifying the emulsion concentrate in or in the presence of water.

As additive 1-20% by weight of a tenside and/or 0.1-5% by weight of a stabilizing agent may be used and the mixture may be preferably filled up to 100% with an organic solvent.

It is preferred to use as tenside a mixture of anionic and non-ionic tensides. The following tensides may be preferably applied: calcium salts of alkyl aryl sulfonic acids, mono and diesters of phosphoric acid, nonyl and tributyl phenol polyglycol ethers, adducts of fatty alcohols and ethylene oxide, fatty acid polyglycol esters, ethylene oxide - propylene oxide block polymers, etc.

As solvent preferably mixtures of aromatic hydrocarbons (e.g. xylenes), cyclohexanol, butanol, methyl ethyl ketone, isopropanol, etc. may be used.

The compositions of the present invention may also comprise further synergists which enable the reduction of the amount of the active ingredient. For this purpose preferably piperonyl butoxide may be applied.

According to a further aspect of the present invention there is provided a process for the preparation of an insecticidal active ingredient comprising out of the eight possible isomers of synthetic pyrethroids of the Formula I (wherein X stands for chlorine or bromine) substantially only a 3:7-5:5 mixture of enantiomer-pairs Ia:Ib—wherein Ia is 1RcicS and 1ScisR and Ib is 1RtransS and 1StransR—which comprises:

f) preparing from a mixture comprising in addition to the isomer-pairs Ia+Ib other possible isomers too and-/or comprising the isomer-pairs Ia+Ib in a ratio other than the desired values a saturated solution with a protic or apolar aprotic inert organic solvent, seeding the solution with a seeding crystal consisting of a 3:7-5:5 mixture of enantiomer-pairs Ia and Ib, and isolating the crystals precipitating at a temperature between 30° C. and −30° C.; or g) seeding a melt of a mixture comprising in addition to the isomer-pairs Ia+Ib other isomers too and/or comprising the isomer-pairs Ia+Ib in a ratio other than the desired value at a temperature between 10° C. and 60° C. with a seeding crystal comprising a 3:7-5:5 mixture of enantiomer-pairs Ia and Ib, allowing the solution to crystallize at a temperature between 30° C. and −10° C. and if desired suspending the mixture thus obtained at a temperature between −10° C. and −20° C. in a protic or apolar aprotic inert organic solvent and isolating the precipitated crystals; or h) adding to a solution or a melt of a mixture comprising in addition to the isomer-pairs Ia+Ib other isomers too and/or comprising the isomer-pairs Ia+Ib in a ratio other than the desired value an enantiomer-pair Ia or Ib in such an amount that the solution or the melt should contain the isomers in a ratio of 3:7-5:5 and if desired performing crystallization according to variant f) or g); or i) admixing enantiomer-pairs Ia and Ib in the desired ratio—if desired in the presence of a protic or apolar aprotic organic solvent—homogenizing the mixture and performing crystallization—if desired after the seeding step according to variant f).

According to variants f) of the process of the present invention one may preferably proceed by using a $C_{1-12}$ hydrocarbon, $C_{1-6}$ chlorinated hydrocarbon, $C_{1-5}$ dialkyl ether or $C_{1-10}$ alcohol as organic solvent. The said solvents may be straight or branched chained, and cyclic and alicyclic, respectively.

It is preferred to carry out seeding with a seeding crystal in the presence of an antioxidant—particularly tertiary butyl hydroxy toluene or 2,2,4-trimethyl-quinoline—and to use methanol, ethanol, isopropanol petrolether or hexane as solvent.

One may proceed preferably by accomplishing crystallization under slow cooling.

According to a preferred form of realization of the process of the present invention a mixture of 60% of trans and 40% of cis cypermethrin enantiomer-pairs (18.2% of Ia, 26.8% of Ib, 21.8% of Ic and 33.2% of Id; referred to as Ie) is used as starting material. The said mixture is dissolved in isopropanol and the solution is seeded with seeding crystals consisting of a mixture of Ia and Ib in the presence of 0.01% of 2,2,4-trimethylquinoline or tertiary butyl hydroxy toluene. A crystalline product is obtained with an absolute yield of 35-40%, which melts at 63.5°-65° C., comprises the enantiomer-pairs Ia and Ib in a ratio of 40:60 and contains enantiomer-pairs Ic and Id as contamination in an amount of 5%. The products thus obtained may be recrystallized as described above. Thus the mixture of enantiomer-pairs Ia and Ib can be prepared with a purity above 99%.

Similar results are obtained when recrystallizing mixtures of other cis/trane ratios.

The cypermethrins used as starting material may be prepared by esterifying the mixture of cyclopropane carboxylic acids of suitable cis/trans ratio.

In the following Table the melting points of mixtures of various cis/tans ratio are disclosed.

| Ia/Ib | 25:75 | 30:70 | 40:60 | 50:50 | 55:45 |
|---|---|---|---|---|---|
| m.p.: °C. | 67–67.5 | 65:68 | 63.5–65 | 60.5–62 | 61.5–64 |

The practical feasibility in the desired direction of the crystallization step strongly depends on the purity of the starting cypermethrin mixture. If the active ingredient content is lower than 95%, the yields decrease. Tarry contaminations may even inhibit crystallization.

The crystallization of the mixture of enantiomer-pairs Ia and Ib according to the present invention may be carried out in the absence of a solvent too. Thus cypermethrin of the composition Ie may be seeded with crystals consisting of Ia and Ib. In a refrigerator the mixture of Ia and Ib precipitates within a week. The crystals are isolated by adding ethanol cooled to −20° C. to the mixture and filtering the crystals.

The mixture of enantiomer-pairs Ia+Ib according to the present invention may also be prepared by admixing and/or crystallizing Ia and Ib or various amounts thereof or by admixing and/or crystallizing a mixture of Ia and Ib, or calculated amount of Ib, respectively.

The biological activity of the products according to the present invention is tested on various insect specii. In the test methods the effect of stereoisomers used as a reference standard and prepared by known methods—e.g. by chromatographical separation or by chromatographical separation of cypermethrins prepared from chiral acids—is disclosed as well.

INDUSTRIAL APPLICABILITY

The insecticidal compositions of the present invention are harmless to the environment and can be used particularly in household and stables for combatting flying insects and pests having a hidden mode of life and also for the treatment of pasture.

MODES OF CARRYING OUT THE INVENTION

Further details of the present invention are to be found in the following chemical and biological examples without limiting the scope of protection to the said Examples.

Further Chemical Examples
EXAMPLE 30

100 g of cypermethrin (consisting according to gas chromatography of a mixture of 18.2% of Ia, 21.8% of Ic, 26.8% of Ib and 33.2% of Id), 0.2 g of potassium hydroxide and 0.2 g of 2,6-di-tertiary butyl-4-methylphenol are dissolved in 2000ml of isopropanol under constant stirring at 45.0° C. The solution is slowly cooled to 30° C., clarified with activated charcoal and filtered at 30° C. The colorless solution is seeded with a crystal consisting of 60% of Ib and 40% of Ia and the mixture is stirred at −10° C. for 24 hours. The precipitated product is filtered, washed with isopropanol and dried in vacuo. Thus 36.02 g of a snow-white crystalline product are obtained, M.p.: 62°–65° C. (non-corrected value). According to GC and TLC analysis the product contains 37% of Ia and 58% of Ib isomers. Yield: 76% (related to the Ia+Ib isomer content of the cypermethrin starting material). Ia isomer $R_f=0.25$; Ib isomer $R_f=0.20$.

After recrystallization from isopropanol 32 g of the product are obtained as first crops. M.p.: 63.5–65.0° C.; the product consists of 39.5 % of Ia and 59.5% of Ib.

IR / KBr / $\nu_{c=o}$ 1730, 1735 cm$^{-1}$

NMR / CDCl$_3$/δ/ ppm/: 1.05–2.45 m /8H/; 5.6, d, J=8Hz /=CH trans 0.6H/; 6.14, d, J=8Hz /=CH cis 0.4H/; 6.35, d, /1H/; 6.85–7.60 m, /9H/

EXAMPLE 30a 36.02 g of crude crystalline cypermethrin prepared according to Example 30 consisting of 37% of Ia and 58% of Ib were recrystallized from 90 ml of methanol. 31.5 g of crystalline cypermethrin consisting of 38.5% of Ia and 60.5% of Ib are obtained. M.p.: 63° C., purity 99%.

EXAMPLE 31

The process of Example 30 is repeated except that the starting materials are dissolved in 1600 ml of methanol. Thus 34.5 g of snow-white crystalline product are obtained M.p.: 62°–64° C. (non-corrected value) According to GC analysis the product contains 37.5 % of Ia and 58.5 % of Ib isomers.

Yield: 76.6 % (related to the Ia and Ib isomer content of the cypermethrine starting material).

EXAMPLE 32

The process of Example 30 is repeated except that the starting materials are dissolved in 2400 ml of n-hexane. Thus 30.5 g of snow-white crystalline product are obtained M.p.: 63° C. (non-corrected value). According to GC analysis the product contains 37.4% of Ia and 57.8% of Ib isomers. Yield: 67.7% (related to the Ia+Ib isomer content of the cypermethrine starting material).

EXAMPLE 33

100 g of cypermethrin (27.8% of Ia, 21.8% of Ib, 32.1% of Ie and 18.2% of Id), 0.2 g of potassium hydroxide and 0.2 g of 2,6-di-tertiary butyl-4-methylphenol are dissolved in 2000 ml of isopropanol under stirring at 45° C. The solution is clarified with activated charcoal and filtered at 30° C. The colorless solution is seeded with a seeding crystal consisting of 20% of Ib and 80% of Ia and stirred at −10° C. for 36 hours. The precipitated product is filtered, washed with isopropanol and dried in vacuo. Thus 30 g of snow-white crystalline product are obtained, m.p.: 66°–73° C. According to gas chromatography the product contains 77% of Ia+19% of Ib, purity 96% (TLC, see Example 1).

After recrystallization from isopropanol as first generation 26.5 g of a snow-white crystalline product are obtained, m.p.: 70°–73° C., containing 81.5 of Ia+18% of Ib (GC analysis).

IR / KBr / $\nu_{c=o}$ 1730 cm$^{-1}$

NMR / CDCl$_3$/δ/ppm/: 1.05–2.45 m /8H/; 5.60 d, J=8Hz /=CH trans 0.2H/; 6.14 d, J=8Hz /=CH cis 0.8 H/; 6.35 d /ArCH 1H/ 6.85–7.60 m /9H/

EXAMPLE 34

100 g of colorless clearly transparent oily cypermethrin (18.2% of Ia, 21.8% of Ic, 26.8% of Ib and 32.2% of Id) are seeded with a seeding crystal consisting of 60% of Ib and 40% of Ia and the solution is allowed to crystallize at 7° C. for a week. The mixture is suspended in 100 ml of a 1:1 mixture of isopropanol and diisopropyl ether and filtered at −15° C. The crystals are washed with isopropanol and dried in vacuo. Thus 40.1 g of a white crystalline product are obtained, containing 37.5% of Ia and 59% of Ib, m.p.: 62.5°–65° C. Yield 86%. After recrystallization from isopropanol as first generation 36 g of a snow-white crystalline product are obtained, m.p.: 63.5°–65° C., consisting of 40% of Ia and 60% of Ib (GC). The IR and NMR are identical with those disclosed in Example 30.

EXAMPLE 35

100 g of cypermethrin (18.2% of Ia, 21.8% of Ic, 26.8% of Ib and 32.2% of Id) and 0.05 g of 2,6-di-tertiary butyl-4-methyl-phenol are dissolved in 100 ml of diisopropyl ether under constant stirring at 0° C. and the solution is clarified with 2 g of activated charcoal. The solution is filtered and seeded at −15° C. with a seeding crystal consisting of 60% of Ib and 40% of Ia. The mixture is allowed to crystallize for 72 hours, the crystals are filtered, washed with diisopropyl ether and isopropanol and dried. Thus 38 g of a snow-white crystalline product are obtained, yield 62°–65° C., comprising 37.5 g % of Ia and 58% of Ib. Yield 80.6%. After recrystallization from isopropanol as first generation 35 g of a snow-white crystalline product are obtained, m.p.: 63.5°–65° C., the ratio for the Ia:Ib isomers=40:60. The physical constants are identical with those disclosed in Example 30.

EXAMPLE 36

10 g of samples of the product obtained according to Example 31 (the ratio of the Ia:Ib isomers=4:1) are admixed with 4.60 g, 6 g, 10 g, 16.67 g and 22.0 g of pure seeding crystals of Ib, respectively, and the mixtures thus obtained are recrystallized as described in Example 30 from a 10-fold amount of isopropanol, each. The composition and melting point of the products thus obtained are shown in the following Table.

| Ia:Ib | M.p.: (°C.) |
|---|---|
| 55:45 | 61.5–64 |
| 5:5 | 60.5–62 |
| 4:6 | 63.5–65 |
| 3:7 | 65–68 |
| 25:75 | 67–71.5 |

Further Formulating Examples

EXAMPLE 37

To 166.2 g of perlite ($d_{max}$=120μm) 0.8 g of synthetic silicic acid (Aerosil 300) are added in a fluidizing rapid stirrer. 20 g of a cypermethrin mixture of enantiomer-pairs Ia:Ib=4:6 and 2 g of fatty alcohol polyglycol ether are added so that the mixture is uniformly homogenized. The powder mixture is ground first in a mechanical mill and afterwards in an air flow mill, whereupon 5 g of octyl phenol polyglycol ether (EO=20) and 2 g of sulfosuccinate are added in a rapid stirrer. The wettable powder mixture (WP) thus obtained is subjected to suspension stability test. Wetting time=23 seconds; floatabilty=89% (standard WHO method).

EXAMPLE 38

3 g of a mixture of cypermethrin enantiomer-pairs Ia:Ib=3:7 and 0.3 g of fatty alcohol polyglycol ether are applied in a homogenizing apparatus onto talc ($d_{max}$=15 μm) adjusted to the pH value of 6.5 with a buffer of 0.8 of synthetic silicic acid (Aerosil 200) and 193.9 g of potassium and sodium phosphate. To the mixture 1 g of dioctyl sulfosuccinate and 1 g of fatty alcohol polyglycol ether sulfonate are added under stirring and the mixture is ground to an average particle size of 20 μm. Thus a thin flowable powder mixture is obtained.

EXAMPLE 39

5 g of a mixture of cypermethrin enantiomer-pairs Ia:Ib=55:45 are dissolved in a mixture of 21.25 g of xylene and 42.5 g of n-propanol under slow stirring. To the solution a mixture of 4 g of ethoxylated alkyl phenol+calcium salt of linear alkyl aryl sulfonate and mixture of 6 g of ethoxylated amine+alkali salt of linear alkyl aryl sulfonate is added under stirring until all the materials are completely dissolved, whereupon 21.25 g of water are added. Thus a transparent solution is obtained which maintains its properties at a temperature between 0° C. and 50° C. for long period of time. The solution can be optionally diluted with water at any rate under the formation of an emulsion having a droplet-size of 0.8–1.5 μm.

EXAMPLE 40

5 g of a mixture of cypermethrin enantiomer-pairs Ia:Ib=25:75 are dissolved in a mixture of 75 g of xylene and 10 g of an aliphatic oil whereupon under slow stirring a mixture (7.5 g) of ethoxylated alkyl phenol+calcium salt of linear alkyl aryl sulfonate and also a mixture (2.5 g) of ethoxylated fatty acid+linear alkyl aryl sulfonate salt are added. When measured according to the method of CIPAC the emulsion concentrate proves to be stable after 170 hours.

EXAMPLE 41

In a mechanical granulator a 50:50 mixture of the Ia and Ib cypermethrin enantiomer-pairs is admixed with 1500 g of polycarboxylate alkali salt, 500 g of sodium dodecyl benzene sulfonate, 500 g of saccharose and 7200 g of China-clay. The powder mixture is admixed with 8300 ml of water by using a stirrer of large shearing strength (v=10 m/sec) and subjected to spray drying. The distribution of particle size is as follows:

0.1–0.4 mm=95%. The floatability amounts to 98% (according to the WHO method).

EXAMPLE 42

Emulsifiable concentrates (EC) are prepared by admixing the following components:

| Component | Amount, kg/kg |
|---|---|
| 10 EC | |
| Isomer-pair Ia:Ib = 40:60 | 0.105 |
| Cyclohexanol | 0.290 |
| Atlox 3386 B | 0.020 |
| Atlox 3400 B | 0.045 |
| Odorless mineral oil | 0.540 |
| 5 EC | |
| Isomer-pairs Ia:Ib = 40:60 | 0.050 |
| Cyclohexanol | 0.290 |
| Atlox 3386 B | 0.020 |
| Atlox 3400 B | 0.045 |
| Odorless mineral oil | 0.595 |

Further Biological Examples

EXAMPLE 43

In Table 1 the activity of various stereoisomers of cypermethrin on the house fly (*Musca domestica*) is shown.

The test is carried out as follows:

The active ingredient is dissolved in a 1:2 mixture of oil and acetone; filter paper discs (Whatman No. 1, diameter 9 cm) are impregnated with the solutions of the corresponding stereoisomers and enantiomer-pairs, respectively. The acetone is allowed to evaporate, whereupon the insects are exposed to filter papers discs placed in Petri-dishes. Three parallels are used on each dose and 15 insects are placed into each Petri-dish. The percental mortality is determined after 24 hours. The corrected percent mortality is calculated by means of the Abbot Formula.

TABLE 11

| Cypermethrin stereoisomers | Dose (mg/disc) | | | | |
|---|---|---|---|---|---|
| | 0.04 | 0.11 | 0.33 | 1.00 | 3.00 |
| | 24 hours' mortality % | | | | |
| If | 68 | 93 | 100 | 100 | 100 |
| Ia | 44 | 84 | 100 | 100 | 100 |
| Ig | 48 | 68 | 83 | 100 | 100 |
| Ib | 32 | 62 | 95 | 100 | 100 |
| Ia:Ib = 40:60 | 41 | 81 | 100 | 100 | 100 |

According to this test the activity of mixture Ia+Ib corresponds to that of the pure isomer Ia.

EXAMPLE 44

It appears from Table 12 that the increased activity shown in Example 41 is due to the synergistic effect of the trans-isomers to Tribolium confusum.

TABLE 12

| Active ingredient | Dose (mg/disc) | | | |
|---|---|---|---|---|
| | 0.11 | 0.33 | 1.00 | 3.00 |
| | 24 hours' mortality % | | | |
| 1ScisR (Ih) | 0 | 38 | 80 | 100 |
| 1RcisS (If) | 80 | 100 | 100 | 100 |
| Ia | 22 | 65 | 94 | 100 |
| 1StransR (Ii) | 0 | 0 | 71 | 90 |
| 1RtransS (Ig) | 70 | 92 | 100 | 100 |
| Ib | 64 | 89 | 100 | 100 |
| Ia:Ib = 40:60 | 61 | 89 | 100 | 100 |

In Example 47 it is shown on further insect species that the enantiomer-pair Ib of the present invention is more active than Ia. The increased activity manifests itself not only in the 24 hour mortality but also in the fact that the toxical effect is exhibited more rapidly.

EXAMPLE 45

In Table 13 the insecticidal effect of mixtures of enantiomer-pairs Ia and Ib of various ratio is shown on flour beetle (*Tribolium confusum*). The test method is that disclosed in Example 43.

TABLE 13

| Ia:Ib | Dose (mg/disc) | | | |
|---|---|---|---|---|
| | 0.02 | 0.06 | 0.25 | 1.00 |
| | 24 hours' mortality % | | | |
| 10:0 | 0 | 14 | 54 | 100 |
| 5:5 | 0 | 43 | 100 | 100 |
| 4:6 | 14 | 53 | 100 | 100 |
| 3:7 | 20 | 81 | 100 | 100 |
| 0:10 | 8 | 46 | 100 | 100 |

The above data clearly prove the synergism between enantiomer-pairs Ia and Ib.

EXAMPLE 46

According to a further recognition of the present invention when the mixtures of enantiomer-pairs Ia and Ib are combined with conventional pyrethroid synergists (e.g. piperonyl butoxide, NIA 16388 etc ) the increase of activity is larger than the usual value (see Example 45.

In Table 14 the activity on Colorado potato beetle is shown.

The test method is as follows:

The test materials are dissolved in 2-ethoxyethanol (Cellosolve). One 0.3 μl drop of the solution is applied to the abdominal sterna of the imago. The treatment is carried out by using 2 parallels and 10 insects for each dose. Mortality is determined after 48 hours.

TABLE 14

| Active ingredient | Dose/μg/beetle | | | |
|---|---|---|---|---|
| | 0.05 | 0.10 | 0.20 | 0.40 |
| | 24 hours' mortality % | | | |
| Ia | 50 | 55 | 75 | 80 |
| Ib | 0 | 25 | 75 | 85 |
| Ia:Ib = 4:6 | 45 | 60 | 70 | 80 |
| Ia:Ib = 3:7 | 45 | 65 | 75 | 85 |
| deltamethrin | 45 | 60 | 75 | 85 |
| cypermethrin | 0 | 20 | 45 | 75 |

Synergism is observed between enantiomer-pairs Ia and Ib, although on imago of Colorado potato beetle Ia is more active than Ib. Mixtures of enantiomer-pairs Ia and Ib exert the same activity as deltamethrin.

EXAMPLE 47

The comparative test of Ia, Ib and a 40:60 mixture of Ia:Ib is carried out on bean weevil (*Acanthoscelides obtectus*), flour-beetle, (*Tribolium confusum*), house fly (*Musca domestica*) and sheep maggot fly (*Lucillia sericata*). The test method described is Example 41. The results are summarized in Table 15.

TABLE 15

| Species | Enantiomer pair | Dose (mg/disc) | | | | | |
|---|---|---|---|---|---|---|---|
| | | 0.02 | 0.07 | 0.22 | 0.67 | 2.0 | 6.0 |
| A. obtectus | Ia | 10 | 37 | 63 | 95 | 100 | 100 |
| (imago) | Ib | 32 | 55 | 87 | 100 | 100 | 100 |

TABLE 15-continued

| Species | Enantiomer pair | Dose (mg/disc) | | | | | |
|---|---|---|---|---|---|---|---|
| | | 0.02 | 0.07 | 0.22 | 0.67 | 2.0 | 6.0 |
| | Ia:Ib = 4:6 | 30 | 55 | 90 | 100 | 100 | 100 |
| T. confusum | Ia | 0 | 18 | 51 | 100 | 100 | 100 |
| (imago) | Ib | 14 | 73 | 100 | 100 | 100 | 100 |
| | Ia:Ib = 4:6 | 16 | 80 | 100 | 100 | 100 | 100 |
| M. domestica | Ia | 36 | 63 | 88 | 100 | 100 | 100 |
| (imago) | Ib | 0 | 18 | 67 | 100 | 100 | 100 |
| | Ia:Ib = 4:6 | 25 | 45 | 85 | 100 | 100 | 100 |
| L. sericata | Ia | 0 | 30 | 29 | 57 | 60 | 65 |
| (imago) | Ib | 22 | 55 | 70 | 75 | 100 | 100 |
| | Ia:Ib = 4:6 | 18 | 50 | 60 | 75 | 100 | 100 |

EXAMPLE 48

Activity of cypermethrin stereoisomer-pairs as function of time on flour beetle (*T. Confusum*).

Flour beetle (*T. confusum*) imagos are exposed in Petri-dishes according to the method described in Example 43. For each dose 3 parallels are used and 15 animals are applied for each parallel test. In each point of time the insects lying on their backs are counted and the percental results are expressed in Table 16.

TABLE 16

| Stereoisomer-pair and enantiomer- | Exposition time (minutes) | Dose (mg/disc) | | | |
|---|---|---|---|---|---|
| | | 011 | 0.33 | 1.00 | 3.00 |
| | | % of insects showing toxic symptoms | | | |
| Ih | 30 | 0 | 0 | 0 | 0 |
| | 60 | 0 | 0 | 0 | 8 |
| | 120 | 0 | 0 | 0 | 67 |
| | 180 | 0 | 0 | 0 | 88 |
| If | 30 | 0 | 0 | 48 | 64 |
| | 60 | 0 | 5 | 84 | 100 |
| | 120 | 0 | 40 | 100 | 100 |
| | 180 | 39 | 61 | 100 | 100 |
| Ia | 30 | 0 | 0 | 0 | 33 |
| | 60 | 0 | 0 | 16 | 88 |
| | 120 | 0 | 14 | 66 | 100 |
| | 180 | 10 | 49 | 100 | 100 |
| Ii | 30 | 0 | 0 | 0 | 15 |
| | 60 | 0 | 0 | 0 | 70 |
| | 120 | 0 | 0 | 0 | 100 |
| | 180 | 0 | 0 | 0 | 100 |
| Ig | 30 | 0 | 0 | 15 | 68 |
| | 60 | 18 | 34 | 98 | 100 |
| | 120 | 30 | 70 | 100 | 100 |
| | 180 | 34 | 84 | 100 | 100 |
| Ib | 30 | 0 | 0 | 47 | 61 |
| | 60 | 0 | 21 | 82 | 100 |
| | 120 | 28 | 100 | 100 | 100 |
| | 180 | 56 | 100 | 100 | 100 |
| Ia:Ib = 4:6 | 30 | 0 | 0 | 50 | 55 |
| | 60 | 15 | 85 | 85 | 100 |
| | 120 | 30 | 100 | 100 | 100 |
| | 180 | 55 | 100 | 100 | 100 |

EXAMPLE 49

Imagos of flour-beetle (*T. confusum*) are treated in an analogous manner to Example 41. As synergist piperonyl butoxide is used in a dose of 0.5 mg/disc.

TABLE 17

| Cypermethrin stereoisomer | Dose (mg/disc) | | | | |
|---|---|---|---|---|---|
| | 0.4 | 0.2 | 0.1 | 0.05 | 0.025 |
| | 24 hours' mortality | | | | |
| Ia | 96 | 53 | 12 | 0 | 0 |
| Ia + PBO | 100 | 58 | 16 | 0 | 0 |
| Ia + Ib | 100 | 90 | 57 | 18 | 0 |
| Ia + Ib + PBO | 100 | 95 | 75 | 43 | 7 |

It may be been that the mixture of enantiomers Ia and Ib can be synergized to a larger extent than enantiomer Ia. (Ia:Ib=4:6).

EXAMPLE 50

The active ingredients are dissolved in 2-ethoxyethanol and the solutions are applied in the form of 0.2 μl droplets onto the back of fall wetworm (*Hyphantria cunea*) of $L_7$-$L_8$ larvae stage. The treated worms are placed on strawberry leaves in Petri-dishes. The test is carried out by using a doses, 2 parallels and 10 insects for each dose. The killed worms are counted after 24 hours and the percental mortality rate is calculated. The results are summarized in Table 18.

TABLE 18

| Active Ingredient | Dose (μg/disc) | | | | |
|---|---|---|---|---|---|
| | 0.023 | 0.047 | 0.094 | 0.188 | 0.375 |
| | 24 hours' mortality | | | | |
| Ia | 40 | 60 | 65 | 80 | 90 |
| Ib | 10 | 15 | 30 | 70 | 80 |
| Ia:Ib = 4:6 | 40 | 50 | 55 | 65 | 75 |
| cypermethrin | 0 | 10 | 25 | 50 | 75 |

EXAMPLE 51

Leaves already infested with mites (*Tetranychus urticae*) were sprayed under Potter Tower. Mortality after 24 hours on the treated leaves was compared with the control.

TABLE 19

| Active ingredient | approx. $LD_{50}$ (ppm) |
|---|---|
| Ia | 0.056 |
| Ib | 0.340 |
| Ia:Ib = 4:6 | 0.060 |
| cypermethrin | 0.120 |
| deltamethrin | 0.185 |

EXAMPLE 52

The 5 EC formulations prepared according to Example 42 are diluted 50x, 100x, 200x, 400x, 800x and 1600x with water and 0.5 ml doses are sprayed onto glass plates. After drying 10 *L. decemlineata* imagos are placed on each glass plate and the insects are covered with Petri-dishes. The tests are carried out by using 6 doses and 3 parallels for each dose. The killed insects are counted after 48 hours. The results are disclosed in Table 20.

TABLE 20

| 5 EC formulation | Dilution | | | | | |
|---|---|---|---|---|---|---|
| | 1600x | 800x | 400x | 200x | 100x | 50x |
| | Mortality % | | | | | |
| Ia | 0 | 27 | 53 | 63 | 87 | 97 |
| Ia:Ib = 4:6 | 0 | 33 | 53 | 73 | 80 | 93 |
| deltamethrin | 7 | 35 | 53 | 67 | 83 | 100 |
| cypermethrin | 0 | 17 | 33 | 50 | 67 | 83 |

EXAMPLE 53

Glass plates are sprayed with 5 EC formulations prepared according to Example 42 in an analogous manner to Example 52. After drying 10 bean weevil (*Acanthoscelides obtectus*) imagos are placed on each plate and the insects are covered with Petri-dishes. The killed insects are counted after 24 hours. The test is carried out with 6 doses by using 3 parallels for each dose. The results are summarized in Table 21.

TABLE 21

| 5 EC formulation | Dilution | | | | | |
|---|---|---|---|---|---|---|
| | 1600x | 800x | 400x | 200x | 100x | 50x |
| | | | Mortality % | | | |
| Ia | 0 | 13 | 27 | 33 | 50 | 70 |
| Ia:Ib = 4:6 | 10 | 17 | 30 | 37 | 53 | 70 |
| deltamethrin | 7 | 13 | 20 | 37 | 57 | 75 |
| cypermethrin | 0 | 3 | 10 | 20 | 45 | 60 |

EXAMPLE 54

15 bean plants infected with green peach aphids (*Myzus persicae*) at 6 days' age are cultivated in each pot. At 12 days' age the strongly and uniformly infected plants are selected and sprayed to run-off with emulsions freshly prepared from the formulation according to Example 42. Treatments are carried out with three doses (active ingredient 2.5, 5 and 10 ppm) and four parallels are used (one pot per parallel). The second, fourth and eighth day after treatment the aphids are swept down from the plants to a white paper with a fine brush and the live insects are counted. The results are disclosed in Table 22.

TABLE 22

| 5 EC Formulations | Concentration (ppm) | Average number of aphids per pot Days after treatment | | |
|---|---|---|---|---|
| | | 2 | 4 | 8 |
| Ia | 2.5 | 44 | 83 | 245 |
| | 5.0 | 22 | 29 | 90 |
| | 10.0 | 8 | 17 | 30 |
| Ia:Ib + 4:6 | 2.5 | 38 | 71 | 251 |
| | 5.0 | 21 | 32 | 82 |
| | 10.0 | 10 | 11 | 21 |
| deltamethrin | 2.5 | 26 | 47 | 137 |
| | 5.0 | 13 | 19 | 29 |
| | 10.0 | 6 | 11 | 23 |
| control | | 1850 | 2780 | 4120 |

EXAMPLE 55

Tomato plants pre-cultivated in pots are sprayed with a suspension of the active ingredient formed with a mixture of acetone and water. The treated plants are placed into isolators and infected with $L_3$ stage *Leptinotarsa decemlineara* larvae. The percental ratio of paralyzed larvae which fall down from the plants is determined after 6 hours. The results are disclosed in Table 23.

TABLE 23

| Concentration (ppm) | Ia | Ia:Ib = 4:6 |
|---|---|---|
| | % ratio of paralyzed larvae | |
| 1000 | 100 | 100 |
| 200 | 100 | 100 |
| 40 | 46 | 75 |
| 8 | 18 | 60 |

EXAMPLE 56

The treatments are performed on a 25 m² plot strongly infected with Colorado potato beetle. 10 plants per plot are specially marked on which the Colorado potato beetles were counted previously. (During assessment of the number of pests only adults of the second Summer generation are taken into consideration, because at the point of time of the test the ratio of larvae of stages $L_3$ and $L_4$ is negligible). Treatment is accomplished on 25 M² plots at a dose of 10 g of active ingredients/ha with aqueous suspensions of the formulations according to Example 37 and three parallels are used. The test is evaluated by counting the leave insects on the marked plants. The average values of three parallel tests are disclosed in Table 24.

TABLE 24

| 5 ME formulation | Average number of live insects/10 plants Time elapsed after treatment (in days) | | | |
|---|---|---|---|---|
| | 0 | 1 | 3 | 9 |
| Ia | 171 | 11 | 9 | 25 |
| Ia:Ib = 4:6 | 213 | 8 | 4 | 22 |
| Deltamethrin | 181 | 7 | 10 | 19 |
| Control | 211 | 206 | 179 | 183 |

EXAMPLE 57

Residual contact test on adults of *Aphidinus matricariae*. Adults of *A. matricariae* are exposed to residues of the active ingredients freshly applied on glass plates forming cages, then the survivors are counted.

Treatment: test product and control treated with water.

Replicates: at least 3. Plot size (net): 1 cage.

Parasites of known age (24 hours) are used.

The products are applied at 5.1 ppm concentration, to each of the glass plates.

10 females of *A. matricariae* are introduced into each cage and supplied with honey as food. The number of females surviving exposure is determined after 1, 5 and 24 hours, in independent runs. Total number of survivors is calculate for each cage.

The results are shown in Table 25.

TABLE 25

| | Concentration | | | |
|---|---|---|---|---|
| | 5 ppm | | 1 ppm | |
| | 1h | 1h | 5h | 24h |
| | | Mortality % | | |
| Ia | 100 | 100 | 100 | 96 |
| Ia:Ib = 4:6 | 100 | 50 | 90 | 63 |
| deltamethrin | 100 | 20 | 100 | 85 |

EXAMPLE 58

Direct contact test on pupae of *A. metricariae*.

Mature pupae of *A. matricariae* on paprika leaves in Petri-dishes are exposed to a direct spray of the active ingredients. Two or three days before emergence paprika leaves with parasitized pupae are used. The leaves are laid on moistened filter paper in a plastic Petri-dish.

Application of treatment: See Example 57.

The pieces of leaf are transferred after treatment to clean Petri-dish bottoms. The trays are stored in a climatic chamber at 20° C. temperature, 70% relative humidity and a light-dark cycle of 16-8 h. Surviving pupae hatch after 2-3 days. The numbers of hatched and dead pupae are counted. Results are shown in Table 26.

TABLE 26

| Active ingredient | Concentration | | | |
|---|---|---|---|---|
| | 33 ppm | 10 ppm | 5 ppm | 1 ppm |
| | | Mortality % | | |
| Ib:Ia = 6:4 | 14.3 | 0 | 0 | 0 |
| Deltamethrin | 75.0 | 33.0 | 0 | 0 |
| Ia | 77.0 | 12.5 | 0 | 0 |

TABLE 26-continued

| Active ingredient | Concentration | | | |
|---|---|---|---|---|
| | 33 ppm | 10 ppm | 5 ppm | 1 ppm |
| | Mortality % | | | |
| control | 0 | 0 | 0 | 0 |

What is claimed is:

1. A process for preparing a synergistic, crystalline product consisting of solely enantiomer pair 1RCisS and 1SCisR and enantiomer pair 1RTransS and 1STransR cypermethrin in a 3:7 to 5:5 crystalline mixture, which comprises the steps of:
   (a) epimerizing an oily melt or a saturated solution of enantiomer pair 1RCisS and 1SCisR and enantiomer pair 1RTransS and 1STransR in a ratio other than 3:7 to 5:5, or a mixture of enantiomer pair 1RCisS and 1SCisR, enantiomer pair 1RTransS and 1STransR together with enantiomer pair 1RCisR and 1SCisS and enantiomer pair 1RTransR and 1STransS, said saturated solution including a protic or apolar, aprotic inert organic solvent by treating said oily melt or saturated solution with an organic or inorganic base at a temperature of −15° C. to 30° C. to precipitate crystals consisting solely of the 1RCisS and 1SCisR and the 1RTransS and 1STransR enantiomer pairs in a 3:7 to 5:5 weight ratio;
   (b) isolating the precipitated crystals consisting solely of the enantiomer pairs 1RCisS and 1SCisR and 1RTransS and 1STransR at −10° to 30° C., optionally after inoculating the reaction mixture with a seeding crystal consisting of a mixture of the enantiomer pairs 1RCisS and 1SCisR and 1RTransS and 1STransR at a weight ratio of 3:7 to 5:5 before crystallization; and
   (c) repeating any of the above steps, if necessary.

2. The process defined in claim 1 wherein according to step (a) the organic solvent is a $C_1$ to $C_{12}$ hydrocarbon, a $C_1$ to $C_6$ chlorinated hydrocarbon, a $C_2$ to $C_6$ dialkyl ether or a $C_1$ to $C_{10}$ alkanol, whereby said solvents may be straight chain, branched chain or cyclic.

3. The process defined in claim 2 wherein according to step (a) cypermethrin isomer pairs 1RCisS and 1SCisR, 1RTransS and 1STransR, 1RCisR and 1SCisS, and 1RTransR and 1STransS are dissolved in a $C_1$ to $C_{10}$ alkanol in the presence of potassium hydroxide as the inorganic base and following seeding with a seed crystal comprising the 1RCisS and 1SCisR and 1RTransS and 1STransR in a weight ratio of 3:7 to 5:5, the product is crystallized.

4. The process defined in claim 1 wherein the seeding with a seeding crystal is carried out in the presence of an antioxidant.

5. The process defined in claim 4 wherein the antioxidant is tertiary butyl hydroxy toluene or 2,2,4-trimethylquinoline.

6. The process defined in claim 2 wherein the organic solvent is methanol, ethanol, petrolether or hexane.

* * * * *